United States Patent [19]
Underwood

[11] Patent Number: 5,943,806
[45] Date of Patent: Aug. 31, 1999

[54] SHARK GUN

[76] Inventor: John V. Underwood, 1197 Smoke Rise La., Tallahassee, Fla. 32311

[21] Appl. No.: 08/982,888

[22] Filed: Dec. 2, 1997

[51] Int. Cl.[6] .............................. F41C 3/00; A01K 81/04
[52] U.S. Cl. ................................. 42/1.14; 43/6; 102/371
[58] Field of Search .................................. 42/1.12, 1.14; 43/6; 102/371

[56] References Cited

U.S. PATENT DOCUMENTS

| | | |
|---|---|---|
| 2,964,031 | 12/1960 | Dotson . |
| 2,981,026 | 4/1961 | Wedrall . |
| 3,274,936 | 9/1966 | Messina et al. . |
| 3,340,642 | 9/1967 | Vasiljevic . |
| 3,626,626 | 12/1971 | Blanc . |
| 4,077,147 | 3/1978 | Donnard et al. ............................... 42/1 |
| 4,503,585 | 3/1985 | Hamel et al. ............................. 42/1.12 |
| 4,541,194 | 9/1985 | Mongiello, Jr. ............................... 43/6 |
| 4,660,315 | 4/1987 | Ferro ............................................. 43/6 |
| 5,499,619 | 3/1996 | Tarta ......................................... 124/57 |
| 5,566,858 | 10/1996 | Ducker, III .................................. 222/3 |

*Primary Examiner*—Charles T. Jordan
*Assistant Examiner*—Denise J. Buckley
*Attorney, Agent, or Firm*—Peter Loffler

[57] ABSTRACT

A shark gun injects a sharpened projectile into a predator and thereafter forces compressed gas into the predator. The shark gun is comprised of a compressed gas holding cylinder, a firing chamber having a plunger that bears the sharpened projectile and a valve that selectively permits the compressed gas to act on the plunger. A trigger actuates the valve.

20 Claims, 4 Drawing Sheets

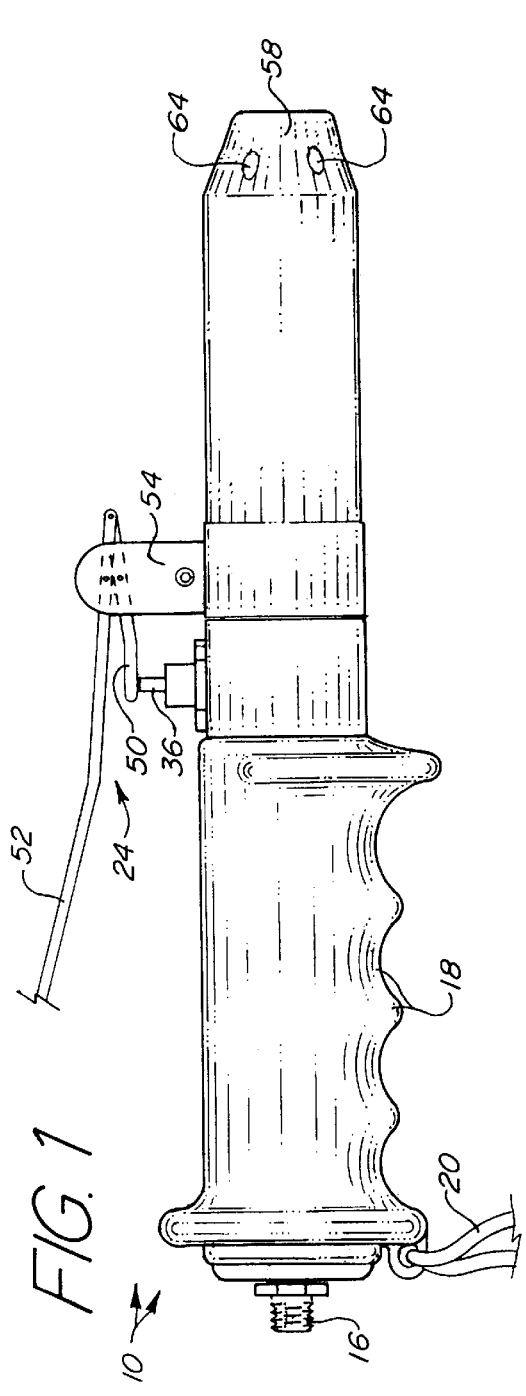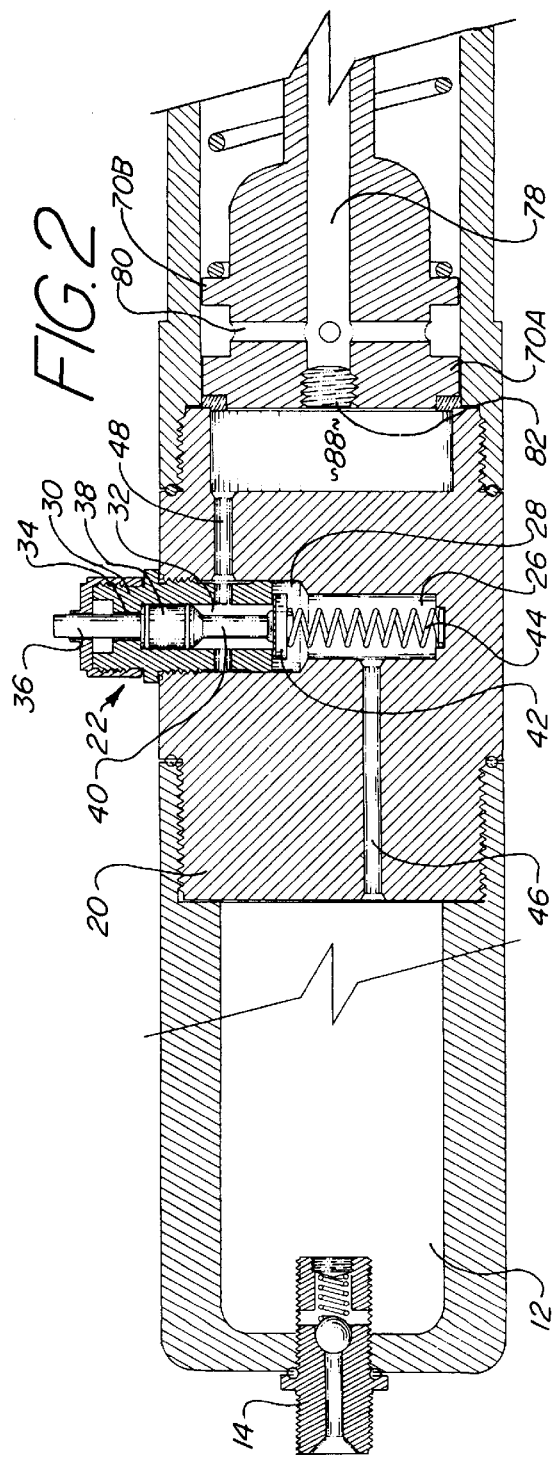

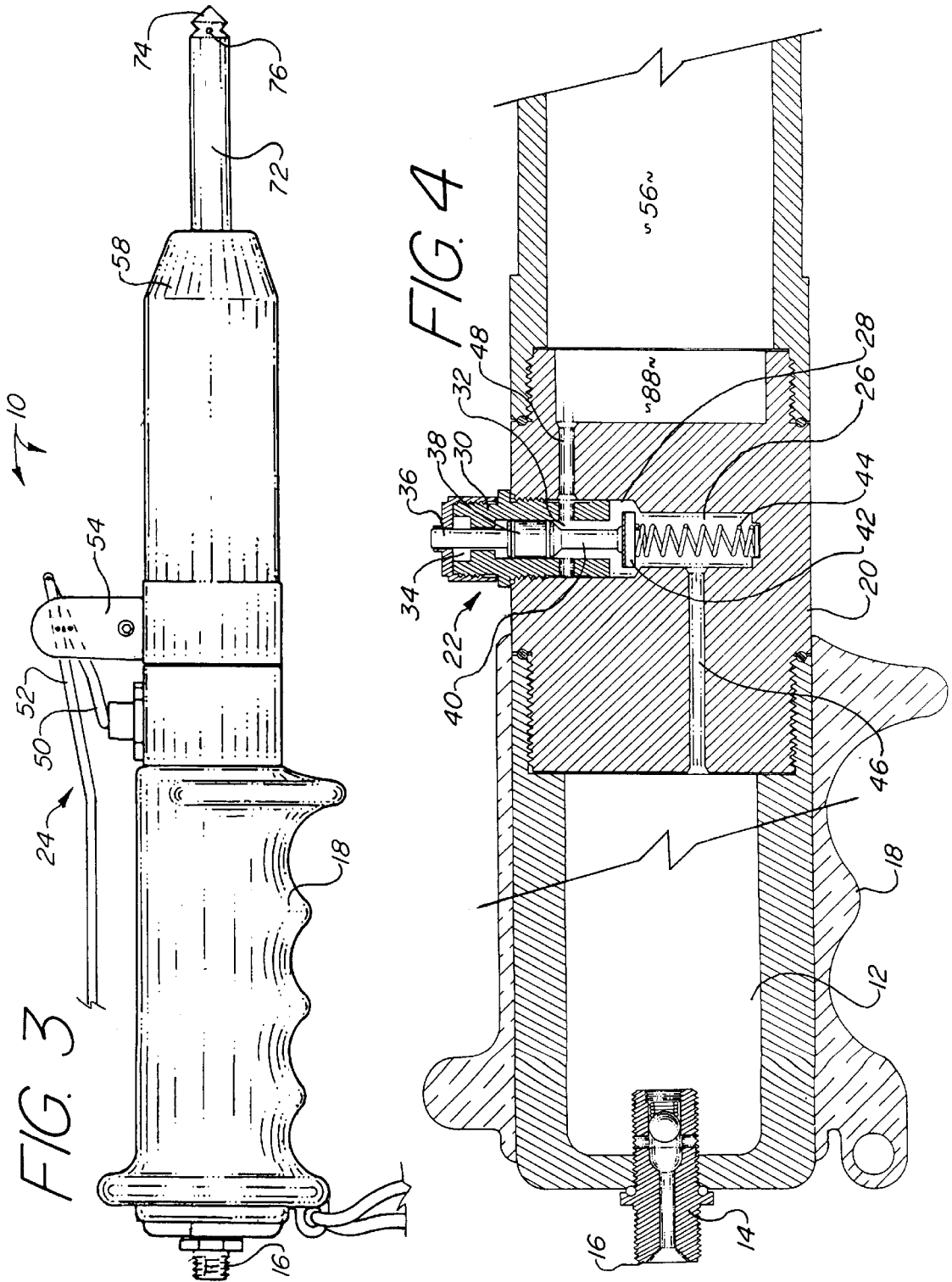

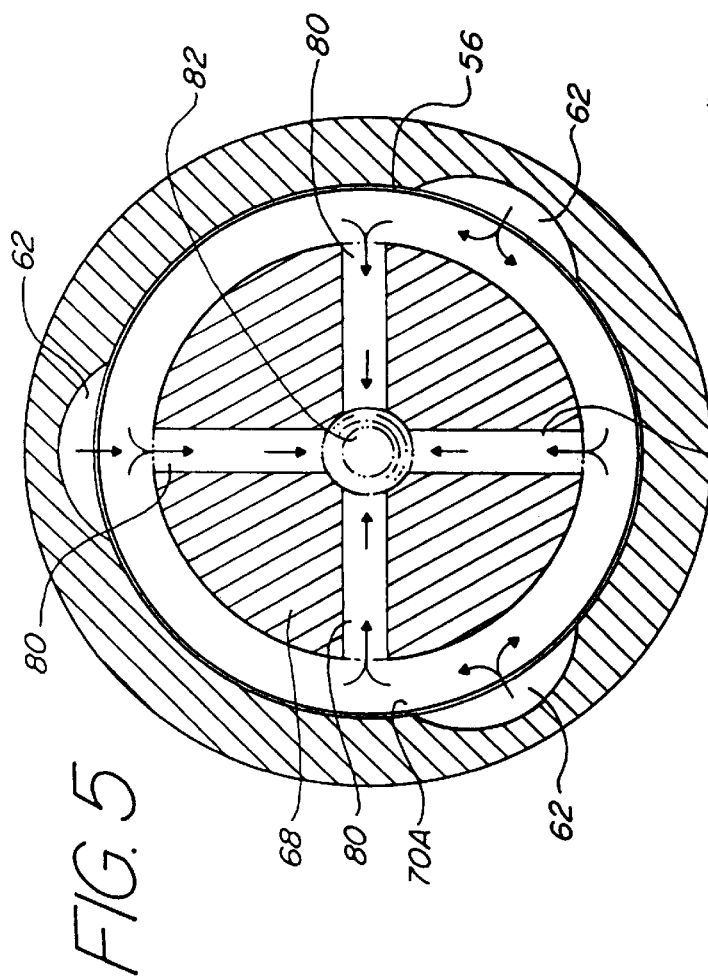
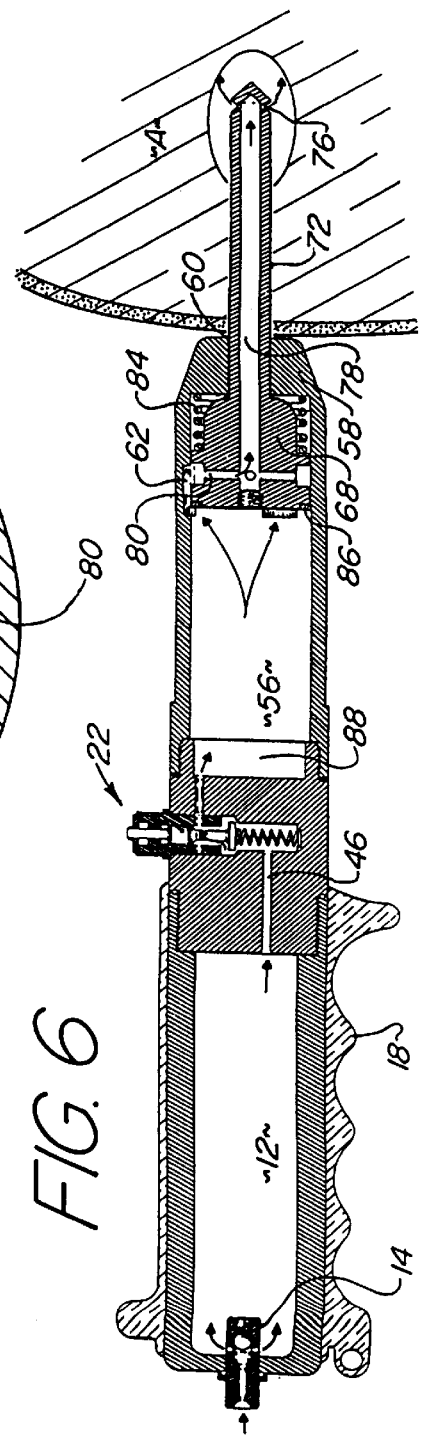
FIG. 5
FIG. 6

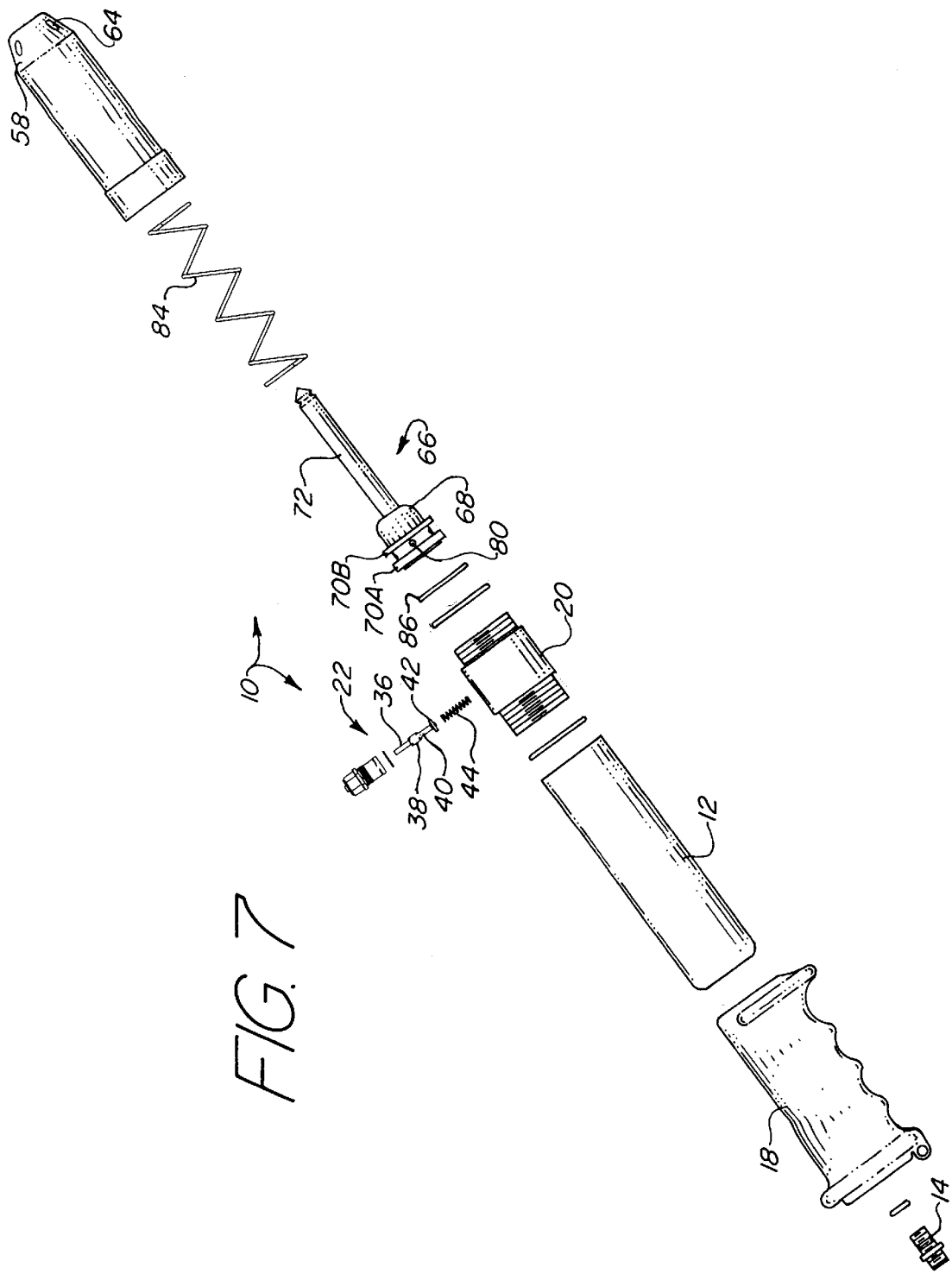

SHARK GUN

BACKGROUND OF THE INVENTION

1. Field of the Invention

The present invention relates to a gun that forces a projectile and compressed gas into a predator.

2. Background of the Prior Art

A major fear of divers is a confrontation with predators, namely sharks. In order to prevent predatory attacks, divers typically carry with them either a chemical repellent or a spear gun. The problem with chemical repellents is that they have limited effectiveness and are not permitted in many ecologically sensitive dive areas. The problem with spear guns is that they are relatively large and may not be maneuvered into position appropriately if the predator comes close in. Furthermore, the spear may strike the predator in a non-sensitive area of the body thereby only wounding the predator which does not terminate the attack. Spear guns are also banned in many dive areas.

Therefore, there is a need in the art for a device that can be carried by divers to defend them against predatory attacks from sharks and similar animals. The device must be of relatively small size so that it can be quickly and easily maneuvered even in a close in attack. The device must be very effective so that if it strikes the animal at all, the animal will immediately terminate the attack. The device must not have any attributes that would cause the device to be banned in dive areas.

SUMMARY OF THE INVENTION

The shark gun of the present invention addresses the aforementioned needs in the art. The shark gun causes a plunger having a sharpened end to rapidly thrust outwardly from the device. Once the plunger is within the animal, a large volume of compressed gas being held within the device is forced into the animal. If the animal manages to survive the plunger and the force of the compressed gas, it will be in no mood to continue the attack.

The shark gun is comprised of a cylinder, a firing chamber, and a valve operated by a trigger. A plunger having a base and a projectile with a sharpened end is adapted to slide within the firing chamber between a retracted position and an extended position. The compressed gas is introduced into and stored within the cylinder. The compressed gas, which will ideally be stored at a pressure greater than 1,000 psi, may come from the diver's tank. The end of the firing chamber is placed against or near the target animal and the trigger is actuated. The trigger causes the valve to open causing the compressed gas to rush from the cylinder into the firing chamber wherein it acts on the plunger and quickly forces the plunger to slide from the retracted position to the extended position with sufficient velocity to penetrate into the animal. Once the plunger is within the animal, the compressed gas escapes through at least one opening located on the sharpened end and into the animal. The large volume of compressed gas entering the animal will cause sufficient damage to the animal so that it will either kill the animal or cause sufficient injury so as to terminate the animal's attack.

The valve is designed to withstand the force created by the compressed gas. The trigger is designed with sufficient mechanical advantage to allow a user to actuate the trigger with relative ease.

BRIEF DESCRIPTION OF THE DRAWINGS

FIG. 1 is a perspective view of the shark gun of the present invention in a retracted position.

FIG. 2 is a partial cutaway view of FIG. 1.

FIG. 3 is a perspective view of the shark gun of the present invention in an extended position.

FIG. 4 is a partial cutaway view of FIG. 3.

FIG. 5 is a front elevation view of the shark gun.

FIG. 6 is a cutaway view of the shark gun deployed within an animal.

FIG. 7 is an exploded view of the shark gun.

Similar reference numerals refer to similar parts throughout the several views of the drawings.

DESCRIPTION OF THE PREFERRED EMBODIMENT

Referring now to the drawings, it is seen that the shark gun of the present invention, generally denoted by reference numeral 10, is comprised of three main sections, the compression chamber, the trigger chamber, and the discharge chamber.

As best seen in FIGS. 2, 4, 6, and 7, the compression chamber is comprised of a cylinder 12 adapted to store compressed gas therein. As illustrated, the compression chamber may be threadably secured to the trigger chamber or may be fixedly attached thereto. As seen, an intake valve 14 of any appropriate design, such as the illustrated ball valve, is located on the end of the cylinder 12 through which to introduce the compressed gas into the cylinder 12. Advantageously, the end 16 of the intake valve 14 will be adapted to receive the discharge nozzle (not illustrated) of a diver's outfit so that a user of the device 10 can fill the cylinder 12 directly from his dive tank. The outer periphery of the compression chamber may be encompassed by a hand grip 18 of any appropriate design for ease of handling by a user and may also have a lanyard attached thereto.

As seen, the trigger chamber is comprised of a housing 20 having a valve 22 that selectively opens and closes gas flow communication between the compression chamber and the discharge chamber and a trigger 24 that operatively engages the valve 22. The valve 22 is seated within a well that has a lower basin 26 and an upper basin 28. The valve 22 has a main body 30 that has a hollow opening passing through its central axis. As seen, the lower portion 32 of the hollow opening has a greater diameter than the diameter of the upper portion 34 of the hollow opening. A shaft 36 passes within the upper portion 34 and has one end attached to a stopper 38 with the other end is attached to the trigger 24. Extending downwardly from the opposing end of the stopper 38 is a shank 40. A plate 42 is attached to the opposing end of the shank 40. A spring 44 has one end abutting the plate 42 and the opposing end abutting the bottom of the lower basin 26, and if desired, this end of the spring 44 can be seated within a groove for greater seating stability of the spring 44. The spring 44 maintains the plate 42 in an abutting position against the main body 30 when the valve 22 is in a normally closed position. A first passageway 46 gas flow connects the cylinder 12 with the lower basin 26 while a second passageway 48 gas flow connects the lower portion 32 with the discharge chamber.

The trigger 24 is comprised of a first rod 50 having one end attached to the top of the shaft and the opposing end pivotally attached to one end of a second rod 52. As seen in FIGS. 1 and 3, the first rod 50 and the second rod 52 are each pivotally attached to a stanchion 54. This double rod with triple pivot point attachment increases the mechanical advantage achieved by the trigger 24. However, it is expressly understood that other trigger designs can be utilized within the scope and spirit of the present invention.

As best seen in FIGS. 6 and 7, the discharge chamber, which can be either threadably or fixedly attached to the trigger chamber, is comprised of a firing chamber 56. The firing chamber 56 is a hollow cylindrical member having a solid end 58 that has an opening 60. A detent 62 encompasses the interior of the firing chamber 56 within its medial portion. At least one portal 64 is located on the firing chamber 56 proximate the solid end 58. A plunger 66 is comprised of a body member 68 having a pair of annular rings 70a and 70b disposed in generally parallel spaced-apart relationship. The annular rings 70a and 70b are sized to snugly fit within the firing chamber 56 and permit the plunger 66 to slide therethrough. If desired, the outer periphery of the annular rings 70a and 70b can have an O-ring made from rubber, silicone or the like. Extending outwardly from the body member 68 is a projectile 72 having a sharpened end 74. As seen, at least one opening 76 is located on the projectile 72 proximate the sharpened end 74. A hollow passageway 78 extends from the at least one first opening 76 and passes through the central axis of the projectile 72 and the central axis of the body member 68. At least one second opening 80 extends from the hollow passageway 78 and terminates at the outer periphery of the body member 68 between the annular rings 70a and 70b. As seen, the end of the hollow passageway 78 has a cap 82 thereon for preventing gas flow through this end (which may have to be open due to manufacturing requirements) of the hollow passageway 78. A spring 84 has one end abutting the solid end 58 and the opposing end abutting the forward positioned annular ring 70b. A stopper 86, made from rubber or similar material is located on the base of the body member 68.

In order to utilize the shark gun 10 of the present invention, the plunger 66 is in a retracted position with the spring 84 maintaining the plunger 66 thereat. In this position, the sharpened end 74 does not clear the solid end 58 and the sharpened end 74 remains fully within the firing chamber 56. Also in this position, a small gas pocket 88 is formed at the end of the firing chamber 56 opposite the solid end 58. Compressed gas is introduced into the cylinder 12 via the intake valve in any desired fashion. Ideally, the gas held within the cylinder 12 will be under pressure at an order of magnitude of 3,000 psi. The device 10 is now armed and ready.

Once needed, the solid end 58 is placed against or near the desired target, such as the body of a shark A or other predatory creature, and the second rod 52 of the trigger 24 is squeezed downwardly toward the device 10. This causes downward articulation of the shaft 36, which in turn causes downward articulation of the shank 40 causing the plate 42 to move downwardly away from main body 30 of the valve 22. The movement of the plate 42 away from its seated position abutting the main body 30 opens gas flow communication between the lower basin 26 and the lower portion 32 and thereby establishes gas flow communication between the compression chamber and the discharge chamber. With gas flow communication established, the compressed gas held within the cylinder 12 rushes through the first passageway 46, through the lower basin 26, through the lower portion 32, and through the second passageway 48 into the pocket 88 of the firing chamber 56. The stopper 38 prevents the gas from passing through to the upper portion 34. The plate 42, by being wider than the lower basin 26 prevents the shaft 36 and shank 40 assembly from being downwardly overextended.

Once within the discharge chamber, the rushing gas pushes against the base of the plunger 66 forcing the plunger 66 to rapidly accelerate forwardly through the firing chamber 56. The plunger 66 continues accelerating until the rearward positioned annular ring 70a is generally aligned with the detent 62. This coincides with the plunger 66 being at maximum extension and abutting the solid end 58. The plunger 66, due to the rapid acceleration caused by the force of the highly compressed gas, penetrates the desired target such as the shark A. As the rearward positioned annular ring 70a is generally aligned with the detent 62, the gas passes around the rearward positioned annular ring 70a and passes through the detent 62, enters the at least one second opening 80, passes through the hollow passageway 78 and through the at least one first opening 76 into the target, thereby completely spoiling the shark's day. The forward positioned annular ring 70b forces the gas into the second opening and prevents the gas from exiting the device 10 through the at least one portal 64. Any water within the discharge chamber is pushed out through the at least one portal 64 by the accelerating plunger 66. Furthermore, the spring 84 diffuses some of the impact force of the plunger 66 against the solid end 58.

Once the valve 22 is closed or once most or all of the gas is released from the device 10, the spring 84 causes the plunger 66 to return to the retracted position.

While the invention has been particularly shown and described with reference to an embodiment thereof, it will be appreciated by those skilled in the art that various changes in form and detail may be made without departing from the spirit and scope of the invention.

I claim:

1. A shark gun comprising:
   a housing
   a cylinder, attached to the housing, for holding compressed gas therein;
   a firing chamber, having a hollow interior and having a first end, a solid second end with a first opening, and a first medial portion, attached to the housing;
   a detent, encompassing the hollow interior within the first medial portion;
   a plunger, having a base with a pair of annular rings and at least one second opening therebetween, a projectile with a sharpened end with at least one third opening and a first hollow passageway extending between the at least one second opening and the at least one third opening, the plunger adapted to slide within the firing chamber between a retracted position within the firing chamber and an extended position wherein the projectile extends from the first opening;
   a valve, operative between a closed position preventing gas flow communication between the cylinder and the firing chamber and an open position permitting gas flow communication between the cylinder and the firing chamber, disposed within the housing; and
   a trigger for articulating the valve between the closed position and the open position.

2. The shark gun as in claim 1 further comprising means for introducing compressed gas into the cylinder.

3. The shark gun as in claim 2 wherein the means for introducing the compressed gas comprises a ball valve.

4. The shark gun as in claim 1 further comprising a hand grip attached to the cylinder.

5. The shark gun as in claim 1 wherein the valve comprises:
   a body having a second hollow passageway, with a lower portion and an upper portion, passing through its central axis;

a basin disposed within the housing;

a shaft having a third end operatively connected to the trigger and a fourth end;

a stopper attached to the fourth end;

a shank having a fifth end attached to the stopper and a sixth end;

a plate, attached to the sixth end, disposed within the basin;

a spring having one end abutting the plate and the opposing end abutting a wall of the basin;

a third hollow passageway gas flow connecting the cylinder and the basin; and a fourth hollow passageway gas flow connecting the lower portion and the firing chamber.

6. The shark gun as in claim 5 wherein the diameter of the lower portion is greater than the diameter of the upper portion.

7. The shark gun as in claim 1 wherein the trigger comprises:

a stanchion attached to the shark gun;

a first rod having a third end attached to the valve, a second medial portion pivotally attached to the stanchion, and a fourth end; and a second rod having a fifth end pivotally attached to the fourth end, a third medial portion pivotally attached to the stanchion, and a sixth end.

8. The shark gun as in claim 1 further comprising at least one fourth opening on the firing chamber proximate the second end.

9. The shark gun as in claim 1 further comprising a spring having a third end abutting the second end and a fourth end abutting the plunger when the plunger is in an extended position.

10. The shark gun as in claim 1 wherein a pocket is defined within the firing chamber between the plunger and the housing whenever the plunger is in a retracted position.

11. A shark gun comprising:

a housing a cylinder, attached to the housing, for holding compressed gas therein;

a firing chamber, having a hollow interior and having a first end, a solid second end with a first opening and at least one second opening, and a first medial portion, attached to the housing;

a detent, encompassing the hollow interior within the first medial portion;

a plunger, having a base with a pair of annular rings and a projectile with a sharpened end, adapted to slide within the firing chamber between a retracted position within the firing chamber and an extended position wherein the projectile extends from the first opening;

a valve, operative between a closed position preventing gas flow communication between the cylinder and the firing chamber and an open position permitting gas flow communication between the cylinder and the firing chamber, disposed within the housing; and a trigger for articulating the valve between the closed position and the open position.

12. The shark gun as in claim 11 further comprising means for introducing compressed gas into the cylinder.

13. The shark gun as in claim 12 wherein the means for introducing the compressed gas comprises a ball valve.

14. The shark gun as in claim 11 further comprising a hand grip attached to the cylinder.

15. The shark gun as in claim 11 wherein the valve comprises:

a body having a second hollow passageway, with a lower portion and an upper portion, passing through its central axis;

a basin disposed within the housing;

a shaft having a third end operatively connected to the trigger and a fourth end;

a stopper attached to the fourth end;

a shank having a fifth end attached to the stopper and a sixth end;

a plate, attached to the sixth end, disposed within the basin;

a spring having one end abutting the plate and the opposing end abutting a wall of the basin;

a third hollow passageway gas flow connecting the cylinder and the basin; and a fourth hollow passageway gas flow connecting the lower portion and the firing chamber.

16. The shark gun as in claim 15 wherein the diameter of the lower portion is greater than the diameter of the upper portion.

17. The shark gun as in claim 11 wherein the trigger comprises:

a stanchion attached to the shark gun;

a first rod having a third end attached to the valve, a second medial portion pivotally attached to the stanchion, and a fourth end; and a second rod having a fifth end pivotally attached to the fourth end, a third medial portion pivotally attached to the stanchion, and a sixth end.

18. The shark gun as in claim 11 further comprising at least one fourth opening on the firing chamber proximate the second end.

19. The shark gun as in claim 11 further comprising a spring having a third end abutting the second end and a fourth end abutting the plunger when the plunger is in an extended position.

20. The shark gun as in claim 11 wherein a pocket is defined within the firing chamber between the plunger and the housing whenever the plunger is in a retracted position.

* * * * *